(12) United States Patent
Pinchuk

(10) Patent No.: US 7,559,949 B2
(45) Date of Patent: Jul. 14, 2009

(54) INJECTABLE INTRAOCULAR LENS THAT MINIMIZES POSTERIOR CAPSULE OPACIFICATION AND METHODS AND MATERIALS FOR REALIZING SAME

(76) Inventor: Leonard Pinchuk, 13704 SW. 92nd Ct., Miami, FL (US) 33176

( * ) Notice: Subject to any disclaimer, the term of this patent is extended or adjusted under 35 U.S.C. 154(b) by 0 days.

(21) Appl. No.: 11/741,239

(22) Filed: Apr. 27, 2007

(65) Prior Publication Data

US 2007/0255404 A1 Nov. 1, 2007

Related U.S. Application Data

(60) Provisional application No. 60/745,941, filed on Apr. 28, 2006.

(51) Int. Cl.
*A61F 2/16* (2006.01)
(52) U.S. Cl. ............... 623/6.56; 424/427; 523/118; 623/6.59
(58) Field of Classification Search ............... 623/6.56, 623/6.59, 6.62; 523/118; 424/427; 128/898
See application file for complete search history.

(56) References Cited

U.S. PATENT DOCUMENTS

| | | | |
|---|---|---|---|
| 4,605,712 A * | 8/1986 | Mueller et al. ............... 525/474 |
| 4,740,534 A | 4/1988 | Matsuda et al. |
| 4,919,151 A * | 4/1990 | Grubbs et al. ............... 128/898 |
| 5,246,979 A * | 9/1993 | Lutz et al. ............... 522/42 |
| 5,278,258 A | 1/1994 | Gerace et al. |
| 5,391,590 A | 2/1995 | Gerace et al. |
| 5,476,515 A * | 12/1995 | Kelman et al. ............... 623/6.59 |
| 5,741,331 A | 4/1998 | Pinchuk |
| 5,977,282 A * | 11/1999 | Ebbrecht et al. ............... 528/29 |
| 6,102,939 A | 8/2000 | Pinchuk |
| 6,197,240 B1 | 3/2001 | Pinchuk |
| 6,361,561 B1 | 3/2002 | Huo et al. |
| 6,413,262 B2 * | 7/2002 | Saishin et al. ............... 606/107 |
| 6,464,999 B1 * | 10/2002 | Huo et al. ............... 424/422 |
| 6,598,606 B2 * | 7/2003 | Terwee et al. ............... 128/898 |
| 6,613,343 B2 | 9/2003 | Dillingham et al. |
| 6,629,947 B1 | 10/2003 | Sahatjian et al. |
| 6,713,583 B2 | 3/2004 | Liao et al. |
| 6,747,090 B2 | 6/2004 | De Groot et al. |
| 6,855,770 B2 | 2/2005 | Pinchuk et al. |
| 6,930,196 B2 * | 8/2005 | Carlson et al. ............... 560/25 |
| 6,986,763 B2 | 1/2006 | Holmen |
| 7,156,101 B2 | 1/2007 | Terwee et al. |
| 7,348,022 B1 * | 3/2008 | Clayton et al. ............... 424/427 |
| 2002/0045706 A1 * | 4/2002 | Houston et al. ............... 525/100 |
| 2005/0125059 A1 | 6/2005 | Pinchuk et al. |
| 2005/0228120 A1 | 10/2005 | Hughes et al. |
| 2006/0106458 A1 * | 5/2006 | Jason et al. ............... 623/6.11 |

FOREIGN PATENT DOCUMENTS

| | | | |
|---|---|---|---|
| EP | 0837084 A2 * | 4/1998 |
| EP | 1106189 | 6/2001 |
| EP | 1364663 A1 * | 11/2003 |
| WO | WO/00/22459 | 4/2000 |
| WO | WO/01/77197 | 10/2001 |
| WO | WO 0247731 A2 * | 6/2002 |
| WO | WO 2004/011529 A2 * | 2/2004 |

OTHER PUBLICATIONS

"Update on Accommodative IOLs", Howard Fine, MD, Michael Colvard, MD, H Burkhard Dick, MD, Cataract & Refractive Surgery Today, downloaded Apr. 4, 2006, www.crstodayarchive.com/03.

* cited by examiner

*Primary Examiner*—Paul Prebilic
(74) *Attorney, Agent, or Firm*—Gordon & Jacobson, PC

(57) ABSTRACT

Polymeric materials and methods that realize a gel-type intraocular lens that is formed in situ within the lens capsule of the eye. The polymeric material of the intraocular lens includes reactive end groups that effectively bond with lens capsule walls, thus eliminating space between the intraocular lens and the lens capsule walls and significantly reducing the proliferation of lens epithelial cells which can cause unwanted posterior capsule opacification.

5 Claims, No Drawings

INJECTABLE INTRAOCULAR LENS THAT MINIMIZES POSTERIOR CAPSULE OPACIFICATION AND METHODS AND MATERIALS FOR REALIZING SAME

CROSS-REFERENCE TO RELATED APPLICATIONS

This application claims the benefit of U.S. Provisional Application No. 60/745,941, filed Apr. 28, 2006, and is related to U.S application Ser. No.11/741,369, entitled "Polymer Adhesive For An Intraocular Lens That Minimizes Posterior Capsule Opacification," filed concurrently herewith, both of which are herein incorporated by reference in their entireties.

BACKGROUND OF THE INVENTION

1. Field of the Invention

This invention relates broadly to artificial lens implants for the eye. More particularly, this invention relates to artificial gel-type lens implants which are formed by injection of a prepolymer into the lens capsule for in situ polymerization.

2. State of the Art

One focus of research in cataract surgery is the replacement of the natural crystalline lens of the eye with a gel-type intraocular lens (IOL) that can adjust with contraction and relaxation of the muscles of the eye. The muscles of the eye that control this adjustment are called the zonules. The ideal gel-type replacement intraocular lens is often referred to as a phako-ersatz lens and it differs from the currently used pseudo-phakic lens in that it can theoretically accommodate over 8 diopters of change, whereas the current generation of pseudo-phakic lenses can accommodate at most 2-3 diopters. An example of a commercially-available pseudo-phakic lens is marketed under the trade name Crystalens™, which move slightly forwards or backwards due to pressure built up in the posterior chamber of the eye.

The natural crystalline lens is a gel-like material that sits within the lens capsule of the eye and when the lens capsule is stretched by the zonules, the gel changes its thickness and therefore its focal point thereby allowing focusing at different distances. The phako-ersatz lens must therefore be a gel or viscous liquid (hereinafter referred to as a "gel") with a relatively fast response time. Children have the ability to accommodate over 15 diopters. People over the age of 45 can generally accommodate between 1 to 3 diopters due to the stiffening of the lens which occurs with age. People over 50 generally accommodate less than 2 diopters. This lack of accommodation is called presbyopia.

It is also desirable that the gel be placed in the eye through a small opening. It is more preferable that the gel be injected in the eye through a needle or cannula as a liquid and then converted into a gel by a polymerization reaction (usually initiated by light). Although there are gels that approach these capabilities, such as silicone-based gels, there have been some extraneous limitations that have prevented their success in the field. One of these limitations has been the well-known problem of posterior capsule opacification (PCO).

When the natural lens is removed from the lens capsule, lens epithelial cells (LECs) begin to multiply and spread on the posterior capsule and effectively render the posterior capsule opaque, which results in impaired vision. The LEC's also spread on the anterior wall. However, due to the large opening in the anterior capsule (the capsulorrhexis), there is no wall for them to spread onto. The occurrence of PCO is relatively high in traditional IOL implantations where the LECs spread between the IOL and the lens capsule. There have been IOL designs where the sharpness of the corners of the lens prevents cellular migration under the lens; however, recent literature suggests that these geometrical features simply retard the progression of PCO. PCO occurs in approximately 40% of IOL recipients within two years of receiving a synthetic lens. The usual treatment for PCO is laser ablation of the posterior capsule where a laser is used to vaporize the posterior capsule and the cells that adhere to it. However, when a gel is present in the capsule, as required for a phako-ersatz-type procedure, the posterior wall cannot be ablated as the gelled lens will extrude out of the capsule. Further the phako-ersatz gel does not have sharp corners to prevent LEC migration. Therefore, the presence of PCO has been a major limiting factor in achieving the phako-ersatz lens. Thus, there is a need for a better material to form a phako-ersatz lens that significantly reduces PCO.

SUMMARY OF THE INVENTION

It is therefore an object of the invention to provide an artificial intraocular lens of a gel-type polymeric material that significantly reduces PCO.

It is another object of the invention to provide such an intraocular lens that chemically bonds to the walls of the lens capsule of the eye in order to limit the invasion of lens epithelial cells between the intraocular lens and the lens capsule and thus significantly reduces PCO.

It is yet another object of the invention to provide such an intraocular lens which is synthesized in-situ by injecting a polymer fluid into the lens capsule, the polymer fluid transformed into a gel-type intraocular lens by a polymerization reaction that takes place in the lens capsule of the eye.

It is still another object of the invention to provide such an intraocular lens wherein the polymer fluid that is injected into the lens capsule is a multi-part polymer including a prepolymer and an initiator that are transformed into a gel-type intraocular lens by a polymerization reaction that takes place in the lens capsule of the eye.

It is yet another object of the invention to provide such an intraocular lens wherein the in situ polymerization reaction that forms the gel-type intraocular lens is initiated (and/or accelerated) by moisture within the lens capsule and/or proteins of the lens capsule of the eye.

It is another object of the invention to provide such an intraocular lens that can adjust with contraction and relaxation of the muscles of the eye, i.e., a phako-ersatz lens.

It is yet another object of the invention to provide polymeric material suitable for injection into the eye to realize such an intraocular lens.

In accord with these objects, which will be discussed in detail below, polymeric materials and methods are disclosed that realize a gel-type intraocular lens that is formed in situ within the lens capsule of the eye. The polymeric material that realizes the intraocular lens includes reactive end groups that effectively bond with lens capsule walls, thus eliminating space between the intraocular lens and the lens capsule walls and significantly reducing the proliferation of lens epithelial cells which can cause unwanted posterior capsule opacification. The polymeric material of the present invention can include i) a prepolymer of polyisobutylene with isocyanate end groups, ii) polyurethanes and polyurethaneureas, iii) epoxides, iv) cyanoacrylates, v) proteinacious polymers, and vi) carbohydrates or polysaccharides as described below in more detail.

Additional objects and advantages of the invention will become apparent to those skilled in the art of ocular implants upon reference to the detailed description.

DETAILED DESCRIPTION OF THE PREFERRED EMBODIMENTS

In accordance with the present invention, a polymeric material is provided that includes end groups that react with the nucleophiles of the lens capsule walls to effectively bond to the lens capsule walls. The nucleophiles of the lens capsule walls can include hydroxyl groups, amine groups, and sulfur groups. If in non-fluid form, the polymeric material can be placed in a fluid form suitable for injection into the lens capsule of the eye. A small capsulorrhexus (preferably of less than 2 mm in diameter) is made in the anterior section of the lens capsule and the natural lens removed by phako emulsification and the like. A miniature diaphragm valve can be placed over the capsulorrhexus and secured in place. The polymeric fluid is injected into the lens capsule of the eye where the polymeric material undergoes a polymerization reaction in situ at the site of the lens capsule. As part of the polymerization reaction, the reactive end groups of the polymeric material react to form the gel-type intraocular lens. Simultaneous to polymerization reaction, the reactive end groups also react with the nucleophiles of the lens capsule walls to effectively bond to the lens capsule walls. The end result is a gel-type intraocular lens that is chemically bound to the lens capsule walls of the eye. The chemical bond between the gel-type intraocular lens and the lens capsule walls limits the invasion of lens epithelial cells therebetween and thus significantly reduces PCO. The polymeric material of the present invention can include i) a prepolymer of polyisobutylene with isocyanate end groups, ii) polyurethanes and polyurethaneureas, iii) epoxides, iv) cyanoacrylates, v) proteinacious polymers, and vi) carbohydrates or polysaccharides as described below in more detail.

Prepolymer of polyisobutylene with isocyanate end groups

In accordance with the present invention, a prepolymer of polyisobutylene with isocyanate end groups is provided. The prepolymer can be bifunctional and linear multifunctional and starred. The isocyanate-terminated prepolymer can be loaded into the first barrel of a two barrel syringe. A reactive co-polymer is loaded into the second barrel of the two barrel syringe. An exemplary reactive co-polymer is a prepolymer of polyisobutylene with hydroxyl or amine end groups. The syringe is preferably realized from polypropylene and is free of air, moisture and any other nucleophile. The isocyanate-terminated prepolymer and the reactive co-polymer are preferably clear with a refractive index between 1.40 and 1.53. The streams from the two barrels of the syringe are merged in a static mixer located on the exit of the syringe. The mixture produced at the exit of the syringe, which is typically a viscous fluid, is injected into the lens capsule through the capsulorrhexus in the anterior section as described above. The isocyanate-terminated prepolymer will spontaneously react with the reactive co-polymer within the lens capsule to form a gel-type intraocular lens. Simultaneous to this polymerization reaction, the reactive isocyanates of the prepolymer component chemically react with the nucleophiles (amine groups) of the lens capsule walls, thereby forming a chemical bond between the gel-type intraocular lens and the lens capsule walls by formation of urea linkage. Such chemical bonding eliminates spaces where lens epithelial cells can migrate and cause PCO. The reaction between the isocyanates of the prepolymer component and the nucleophiles (amine groups) of the lens capsule walls does not produce a byproduct that can otherwise be toxic to the eye. The resultant polymer of the gel-type intraocular lens is preferably clear with a refractive index between 1.40 and 1.53. In the preferred embodiment, the gel-type intraocular lens accommodates with contraction and relaxation of the muscles of the eye and thus operates as a phako-ersatz lens.

Alternatively, the isocyanate-terminated prepolymer and the reactive co-polymer can be premixed prior to loading into a syringe and the contents injected into the lens capsule. In this embodiment, slow reacting components must be used to enable flow through the syringe prior to polymerization.

Polyurethanes and Polyurethaneureas

Polyurethanes and polyurethaneureas are typically comprised of at least two components: an isocyanate-terminated prepolymer and a multinucleophilic co-polymer. An example of a polyurethane is the combination of a multiisocyanate such as the reaction product of a branched polytetramethylene macroglycol reacted with methylene bisphenyl diisocyanate (MDI) to provide a prepolymer that is isocyanate terminated. The multinucleophilic co-polymer can be the same macroglycol, such as polytetramethylene glycol that is terminated with hydroxyl groups. The hydroxyl groups of the multinucleophilic co-polymer react with the isocyanate groups of the multiisocyanate to produce a high molecular weight polyether urethane. This polyether urethane can be tailored to provide specific properties by adding chain extenders to the nucleophilic component of the polymer system, such as ethylene glycol and the like. Some polyurethanes are more stable than others in the body. U.S. Pat. No. 5,133,742, the details of which are herein incorporated by reference in its entirety, describes methods for increasing the biostability of these polymers.

In accordance with the present invention, a low molecular weight isocyanate-terminated prepolymer can be synthesized and loaded into the first barrel of a two barrel syringe. A hydroxyl-terminated co-polymer is loaded into the second barrel of the two barrel syringe. The streams from the two barrels of the syringe are merged in a static mixer (e.g., baffles) located on the exit of the syringe. The mixture produced at the exit of the syringe, which is typically a viscous fluid, is injected into the lens capsule through the capsulorrhexus in the anterior section as described above. The isocyanate-terminated prepolymer and the hydroxl-terminated co-polymer are preferably clear with a refractive index between 1.40 and 1.53. The isocyanate-terminated prepolymer will react spontaneously with the hydroxyl-terminated co-polymer within the lens capsule to form a gel-type intraocular lens. Simultaneous to this polymerization reaction, the reactive isocyanates of the prepolymer component chemically react with the nucleophiles of the lens capsule walls, thereby forming a chemical bond between the gel-type intraocular lens and the lens capsule walls. Such chemical bonding eliminates spaces where lens epithelial cells can migrate and cause PCO. The resulting gel-type intraocular lens is preferably clear with a refractive index between 1.40 and 1.53. In the preferred embodiment, the gel-type intraocular lens accommodates with contraction and relaxation of the muscles of the eye and thus operates as a phako-ersatz lens.

Alternatively, the isocyanate-terminated prepolymer and the hydroxyl-terminated co-polymer can be premixed prior to loading into a syringe and the contents injected into the lens capsule. In this embodiment, slow reacting components must be used to enable flow through the syringe prior to polymerization.

An exemplary hydroxyl-terminated co-polymer that can be used in this capacity is a polyisobutylene (PIB) diol as it will provide a rubbery polyurethane-based gel that is biostable. Other hydroxyl-terminated co-polymers are perfluropolyethyleneglycol polytetramethyleneglycol, poly(hexamethylene carbonate)diol, and the like. Preferably the macroglycol is biostable and has an index of refraction between 1.40 and 1.53.

Epoxies

Epoxies function in a manner similar to polyurethanes but include an epoxide-terminated prepolymer (rather than the isocyanate-terminate prepolymer) and a multinucleophilic co-polymer. The epoxide-terminated prepolymer and the multinucleophilic co-polymer are mixed and the resulting mixture is injected into the lens capsule through the capsulorrhexus in the anterior section as described above. The epoxide-terminated prepolymer will react with the multinucleophilic co-polymer within the lens capsule to form a gel-type intraocular lens. Simultaneous to this polymerization reaction, the reactive epoxide groups of the prepolymer component chemically react with the nucleophiles of the lens capsule walls, thereby forming a chemical bond between the gel-type intraocular lens and the lens capsule walls. Such chemical bonding eliminates spaces where lens epithelial cells can migrate and cause PCO. In the preferred embodiment, the gel-type intraocular lens accommodates with contraction and relaxation of the muscles of the eye and thus operates as a phako-ersatz lens.

Suitable epoxies include glycidyl-terminated polytetramethylene glycol, glycidyl-terminated polyisobutylene, glycidyl terminated perfluroethyleneoxide, and the like.

In an exemplary embodiment, two barrels of a syringe are loaded with an epoxide-terminated prepolymer (Part A) and a nucleophile reactant (Part B), respectively. The streams from the two barrels of the syringe are merged in a static mixer located on the exit of the syringe. The mixture produced at the exit of the syringe, which is typically a viscous fluid, is injected into the lens capsule for in situ polymerization into a gel over a few minutes. Such polymerization forms a gel-type intraocular lens. Simultaneous to this polymerization reaction, the reactive epoxides of the prepolymer component (part A) will chemically react with the nucleophiles of the lens capsule walls, thereby forming a chemical bond between the gel-type intraocular lens and the lens capsule walls. Such chemical bonding eliminates spaces where lens epithelial cells can migrate and cause PCO. The epoxide-terminated prepolymer and the nucleophile reactant as well as the resulting gel-type intraocular lens are preferably clear with a refractive index between 1.40 and 1.53. In the preferred embodiment, the gel-type intraocular lens accommodates with contraction and relaxation of the muscles of the eye and thus operates as a phako-ersatz lens.

Alternatively, the epoxide-terminated prepolymer and the multinucleophilic co-polymer epoxy can be premixed prior to loading into a syringe and the contents injected into the lens capsule. In this embodiment, a slow reacting epoxy, such as the 5 minute epoxies, must be used to enable flow through the syringe prior to polymerization.

Cyanoacrylates (CA)

In accordance with the invention, a polymeric material with cyanoacrylate end groups is provided that readily transforms to a soft rubbery gel (e.g., shore A=20) in the lens capsule upon contact with moisture and/or proteins within the lens capsule to form a gel-type intraocular lens. Simultaneous to this polymerization reaction, the reactive cyanoacrylate groups chemically react with the nucleophiles of the lens capsule walls, thereby forming a chemical bond between the gel-type intraocular lens and the lens capsule walls. Such chemical bonding eliminates spaces where lens epithelial cells can migrate and cause PCO. The cyanoacrylate-terminated polymer as well as the resulting gel-type intraocular lens are preferably clear with a refractive index between 1.40 and 1.53. In the preferred embodiment, the gel-type intraocular lens accommodates with contraction and relaxation of the muscles of the eye and thus operates as a phako-ersatz lens.

Suitable cyanoacrylate (CA) terminated materials that yield soft rubber-like gels upon contact with moisture and/or proteins within the lens capsule include:
  i) 3-arm star cyanoacrylate (CA)-telechelic PIB [Ø(PIB-CA)$_3$];
  ii) CA-PDMS-CA where PDMS is poly(dimethyl siloxane);
  iii) CA-PEG-CA where PEG is polyethylene glycol; and
  iv) CA-PEG-b-PDMS-b-PEG-CA.

A liquid form cyanoacrylate-based material (such as liquid CA-PDMS-CA) can be used as such (in bulk). Preferably, it is loaded into a syringe and injected into the lens capsule from the syringe. Alternatively, a non-fluid form cyanoacrylate-based material (such as crystalline PEG-based material) is preferably dissolved in a suitable solvent (such as DMSO, a non-protic, biocompatible FDA approved solvent) to render the prepolymer injectable. The cyanoacrylation method seems to be of general applicability and can be used for the cyanoacrylation of a great variety of hydroxide-containing molecules.

Aromatic silicone cyanoacrylates can also be used which have a higher refractive index. A PIB-based cyanoacrylate material can also be used. Such material has an even higher refractive index.

A table of other potential cyanoacrylate-based materials follows below. An initiator component (e.g., N,N-dimethyl-p-toluidine in n-$C_6H_{14}$) can also be mixed with a cyanoacrylate-based material to ensure completeness of the reaction that forms the gel-type intraocular lens. The Fn number in the chart below represents the functionality number of the polymer material and relates to the number of end groups per mole of the polymer material.

| Polymers | Visual appearance | MW (g/mol) | $F_n{}^a$ | Initiator | Remarks | Swelling test | Softness |
|---|---|---|---|---|---|---|---|
| CA—PIB—CA<br>\|<br>CA | light brown, highly, viscous, not injectable by syringe | 4000 | 2.5 | N,N-dimethyl-p-toluidine in n-$C_6H_{14}$ | crosslinks upon contact with initiator sol fraction 15% in THF | 108% in hexanes | too soft to measure even by Shore A |

-continued

| Polymers | Visual appearance | MW (g/mol) | $F_n^a$ | Initiator | Remarks | Swelling test | Softness |
|---|---|---|---|---|---|---|---|
| | | | | egg yolk | crosslinks (hard to separate egg yolk and polymer) | | |
| CA—PIB—CA<br>\|<br>CA | light brown, low viscosity liquid, flows freely, injectable by syringe | 1330 | 2.9 | N,N-dimethyl-p-toluidine in n-$C_6H_{14}$ | crosslinks during storage within 2-3 days, sol fraction 5% in THF | 37% in hexanes | Shore A = 40 |
| CA-PDMS-CA | light brown, low viscosity liquid, flows freely, injectable by syringe | 5000 | 1.9 | glass surface (moisture)<br>N,N-dimethyl-p-toluidine in n-$C_6H_{14}$ | crosslinks during storage within 2-3 days<br>crosslinks during storage within 2-3 days, sol fraction 10% in THF | 360% in hexanes | too soft to measure even by Shore A |
| | | | | egg yolk | crosslinks (hard to separate egg yolk and polymer) | | |
| | | | | glass surface (moisture) | crosslinks during storage within 2-3 days, sticks to glassware | | |
| CA-PEG-CA | brown solid | 2000 | 1.9 | glass surface (moisture) | soluble in DMSO, solution syringible, crosslinks upon contact with moisture, crosslinks during storage in less than 1 hr, becomes rubbery upon DMSO addition, solubility limit in DMSO: 50 wt % | 1010% (in water) 612% (in DMSO) | too soft to measure even by Shore A |
| CA-PEG-PDMS-PEG-CA | light brown, low viscosity liquid, flows freely, injectable by syringe | 4000 (PDMS = 40%) | 0.8 | N,N-dimethyl-p-toluidine in THF | crosslinks experiment to be repeated with $F_n$~2.0 triblock | | THF extracted product: too soft to measure even by Shore A |

Proteinacious Polymers and Carbohydrates or Polysaccharides

Proteinacious polymers can also be used in this invention. Here, slurries of collagen, elastin, and/or other peptides can be mixed with one or more cross-linking agents (such as formaldehyde, gluteraldehyde, carbodiimide and the like) and injected into the lens capsule through the capsulorrhexis in the anterior section as described above. The cross-linking agent reacts with the proteinacious polymer to form a gel-type intraocular lens. Simultaneous to this cross-linking reaction, the cross-linking agent chemically reacts with the nucleophiles of the lens capsule walls, thereby forming a chemical bond between the gel-type intraocular lens and the lens capsule walls. Such chemical bonding eliminates spaces where lens epithelial cells can migrate and cause PCO. The proteinacious polymer and the cross-linking agent(s) as well as the resulting gel-type intraocular lens are preferably clear with a refractive index between 1.40 and 1.53. In the preferred embodiment, the gel-type intraocular lens accommodates with contraction and relaxation of the muscles of the eye and thus operates as a phako-ersatz lens.

Similarly, carbohydrate or polysaccharide gel-like materials can be used for this purpose. Such gel like materials can include alginate, pectin, carrageenan, gellan, starch and the like. The gel like materials are mixed with one or more cross-linking agents (such as multivalent cations including calcium chloride, barium chloride and the like; more permanent cross-linking agents can also be used including the epoxides and the multiisocyanates as described above). This mixture is injected into the lens capsule through the capsulorrhexis in the anterior section as described above. The cross-linking agent reacts with the gel-like material to form a gel-type intraocular lens. Simultaneous to this cross-linking reaction, the cross-linking agent chemically reacts with the nucleophiles of the lens capsule walls, thereby forming a chemical bond between the gel-type intraocular lens and the lens capsule walls. Such chemical bonding eliminates spaces where lens epithelial cells can migrate and cause PCO. The carbohydrate or polysaccharide gel-like materials and the cross-linking agent(s) as well as the resulting gel-type intraocular lens are preferably clear with a refractive index between 1.40 and 1.53. In the preferred embodiment, the gel-type intraocular lens accommodates with contraction and relaxation of the muscles of the eye and thus operates as a phako-ersatz lens.

There have been described and illustrated herein several embodiments of polymeric material that can be injected into the lens capsule of the eye to form a gel-type intraocular lens in situ. The polymeric material includes reactive end groups that react to form the gel-type intraocular lens within the lens capsule of the eye. The reactive end groups of the polymeric material also react with the nucleophiles of the lens capsule walls to effectively bond to the lens capsule walls. While particular embodiments of the invention have been described, it is not intended that the invention be limited thereto, as it is intended that the invention be as broad in scope as the art will allow and that the specification be read likewise. For example, mixtures of the polymer materials described herein with similar end groups can be used to realize the gel-type intraocular lens in situ. Moreover, the aforementioned polymers may be used in conjunction with a lens capsule where the capsulorrhexis is closed with a patch. It will therefore be appreciated by those skilled in the art that yet other modifications could be made to the provided invention without deviating from its spirit and scope as claimed herein.

What is claimed is:

1. A method for forming an intraocular lens within a lens capsule of an eye, said method comprising:
    injecting a polymeric material within the lens capsule, wherein the polymeric material is formed from an isocyanate-terminated prepolymer and a reactive co-polymer, the isocyanate-terminated pre-polymer having isocyanate end groups that spontaneously react with the reactive co-polymer within the lens capsule to form a gel that is configured as an intraocular lens therein, the isocyanate end groups also reacting with the nucleophiles of the lens capsule walls to effectively bond to the lens capsule walls, and the isocyanate-terminated prepolymer further comprising polyurethane or polyisobutylene.

2. A method according to claim 1, wherein:
the nucleophiles of the lens capsule walls include hydroxyl groups, amine groups, or sulfur groups.

3. A method according to claim 1, wherein:
the chemical bond between the gel of the intraocular lens and the lens capsule walls limits the invasion of lens epithelial cells therebetween and thus significantly reduces posterior capsular opacification.

4. A method according to claim 1, wherein:
the isocyanate-terminated prepolymer further comprises a polyurethane.

5. A method according to claim 1, wherein:
the isocyanate-terminated prepolymer further comprises polyisobutylene.

* * * * *